(12) United States Patent
Wu et al.

(10) Patent No.: US 11,214,840 B2
(45) Date of Patent: Jan. 4, 2022

(54) METHODS FOR TREATING PERIODONTAL DISEASES

(71) Applicant: NATIONAL CHENG KUNG UNIVERSITY, Tainan (TW)

(72) Inventors: Ping-Ching Wu, Tainan (TW); Dar-Bin Shieh, Tainan (TW); Fong-Yu Cheng, Tainan (TW); Yuh-Ling Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 185 days.

(21) Appl. No.: 16/594,072

(22) Filed: Oct. 7, 2019

(65) Prior Publication Data

US 2020/0172961 A1    Jun. 4, 2020

Related U.S. Application Data

(63) Continuation-in-part of application No. 16/205,236, filed on Nov. 30, 2018, now Pat. No. 10,487,331.

(51) Int. Cl.
| | | |
|---|---|---|
| *C12Q 1/689* | (2018.01) | |
| *A61N 5/06* | (2006.01) | |
| *A61C 1/08* | (2006.01) | |
| *A61C 5/30* | (2017.01) | |

(52) U.S. Cl.
CPC .............. *C12Q 1/689* (2013.01); *A61C 1/088* (2013.01); *A61C 5/30* (2017.02); *A61N 5/062* (2013.01); *A61N 5/0603* (2013.01); *A61N 5/0624* (2013.01); *A61N 2005/0606* (2013.01); *A61N 2005/0659* (2013.01); *A61N 2005/0663* (2013.01)

(58) Field of Classification Search
None
See application file for complete search history.

(56) References Cited

U.S. PATENT DOCUMENTS

| | | | | |
|---|---|---|---|---|
| 2009/0093470 A1* | 4/2009 | Loebel | .............. | A61K 41/0057 514/224.8 |
| 2012/0270177 A1* | 10/2012 | Nakashima | ............ | A61C 17/20 433/86 |
| 2017/0367951 A1* | 12/2017 | Mizumoto | ............... | A61K 8/63 |

\* cited by examiner

*Primary Examiner* — Tracy Vivlemore

(57) ABSTRACT

Provided herein are aptamers that bind specifically to the surface proteins of periodontal pathogens. Also provided herein are methods for detecting and treating periodontal disease in a subject. The method comprises detecting bacteria associated with periodontal disease by use of the present aptamers to analyze a sample taken from a gum pocket of a tooth of the subject; and treating the periodontal disease of the subject by administering to the gum pocket of the tooth a bactericide or an anti-microbial phototherapy to eradicate the bacteria associated with periodontal disease.

14 Claims, 5 Drawing Sheets

Specification includes a Sequence Listing.

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: synthesized

<400> SEQUENCE: 1
tgtaactggg agcggaccta ggttacatga                                    30

<210> SEQ ID NO 2
<211> LENGTH: 30
<212> TYPE: DNA
<213> ORGANISM: Artificial Sequence
<220> FEATURE:
<223> OTHER INFORMATION: synthesized

<400> SEQUENCE: 2
cgtatgtgta cccggtgggg cgcgattgac                                    30
```

```
<210> SEQ ID NO 3
<211> LENGTH: 16
<212> TYPE: DNA
<213> ORGANISM: Artificial Sequence
<220> FEATURE:
<223> OTHER INFORMATION: synthesized

<400> SEQUENCE: 3
tccctacggc gctaac                                                    16

<210> SEQ ID NO 4
<211> LENGTH: 16
<212> TYPE: DNA
<213> ORGANISM: Artificial Sequence
<220> FEATURE:
<223> OTHER INFORMATION: synthesized

<400> SEQUENCE: 4
gccaccgtgc tacaac                                                    16

<210> SEQ ID NO 5
<211> LENGTH: 62
<212> TYPE: DNA
<213> ORGANISM: Artificial Sequence
<220> FEATURE:
<223> OTHER INFORMATION: synthesized

<400> SEQUENCE: 5
tccctacggc gctaactgta actgggagcg gacctaggtt acatgagcca ccgtgctaca    60
ac                                                                   62

<210> SEQ ID NO 6
<211> LENGTH: 62
<212> TYPE: DNA
<213> ORGANISM: Artificial Sequence
<220> FEATURE:
<223> OTHER INFORMATION: synthesized

<400> SEQUENCE: 6
tccctacggc gctaaccgta tgtgtacccg gtggggcgcg attgacgcca ccgtgctaca    60
ac                                                                   62
```

METHODS FOR TREATING PERIODONTAL DISEASES

CROSS-REFERENCE TO RELATED APPLICATION

This application is a continuation-in-part application of U.S. application Ser. No. 16/205,236 filed Nov. 30, 2018, the content of which is hereby incorporated by reference in its entirety.

BACKGROUND OF THE INVENTION

1. Field of the Invention

The present disclosure relates to diagnosing and treating periodontal disease.

2. Description of Related Art

Periodontal disease, such as periodontitis, is the major affliction of the human dentition. In periodontal disease, there is usually a large accumulation of bacteria in plaque attached to the tooth, both above (supragingival) and below (subgingival) the gum line. The plaque can become calcified in its depths, forming what is known as calculus. This calculus deposit and associated plaque can create a "pocket" between tooth and gum, which is characteristic of the disease. The progress of periodontal disease is thought to be a chronic inflammatory response to subgingival bacteria, resulting in the destruction of the tooth's supportive tissues. It is cyclic in its behavior and may remain unnoticed in its early phase.

Pathogenic bacteria involved in the appearance and progression of periodontal disease include, but are not limited to, *Porphyromonas gingivalis*, *Bacteroides forsythus*, *Aggregatibacter actiomycetemcomitans*, *Actinobacillus actinomycetemcomitans*, *Triponema denticola* and *Prevotella intermedia*. Active bacteria produce virulent products, such as toxins and enzymes, to help its survival in the periodontal pocket. During periods of elevated bacterial activity, these virulent products contribute to the destruction of the tooth's supportive tissues, and the reduction in the host's defense system.

Nowadays dentists assess periodontitis by measuring the probing depth of the periodontal pocket, examining X-ray images of the tooth attachment to the alveolar bone and refers to bleeding on probing. Risk factors include smoking habits, stress and family history of periodontitis. Current method relies heavily on the subjective expertise of the dentist. However, probing pocket depth is only a measurement of the historical attachment loss, thus rendering little help in the actual occurrence of periodontitis of the future progression thereof. Bleeding on probing may indicate a healing process instead of a destructive one. Radiographic evaluation have to combine with detail clinical observation in order to give an accurate diagnosis. Occasionally, a microbiological sample is taken and sent to a lab for analysis either by cultivation or DNA technique. However, it takes at least a week of time to produce the result.

In view of the state of the present art, there is a need of a reliable, rapid and inexpensive test system and/or method for identifying the presence of periodontal pathogens. There is also a need for a test system and/or method that can be performed easily and conveniently by a dentist and/or clinician. Such test system and/or method would be of significant value in advising a patient of his or her conditions, choosing suitable treatment for the patient, as well as monitoring the effectiveness of the treatment.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure aims to overcome drawbacks of the prior art and to provide probes and/or kits, which comprise aptamers specifically bind to surface proteins of periodontal pathogens. Thus, the present invention can be used to help dentists and dental hygienists to determine whether their patients are infected with periodontal pathogens, or to monitor the progress of a periodontal treatment. Accordingly, the present disclosure also aims to provide methods for detecting periodontal pathogens (e.g., *P. gingivalis* or *A. actiomycetemcomitans*) in samples obtained from the mouth of a patient without the need to culture a bacterial specimen. The probes, kits and/or methods of the present disclosure may be used for screening suspected teeth, to follow up previous treatment, to choose the right kind of antibiotics and to communicate with the patients the importance of good everyday dental hygiene.

In the first aspect of the present disclosure, isolated aptamers specifically bind to surface proteins of bacteria associated with periodontal disease are provided.

According to one preferred embodiment, the isolated aptamer is characterized in having a first polynucleotide sequence of SEQ ID NO: 1. Additionally and optionally, the isolated aptamer may further comprise a second and third polynucleotide sequences of SEQ ID NOs: 3 and 4 respectively disposed at the upstream and downstream of the first polynucleotide sequence, and thereby gives rise to a polynucleotide of SEQ ID NO: 5. According to preferred embodiments of the present disclosure, the polynucleotide of SEQ ID NO: 5 specifically binds to surface proteins of *Prophyromonas gingivalis* (*P. gingivalis*).

According to another preferred embodiment, the isolated aptamer is characterized in having a fourth polynucleotide sequence of SEQ ID NO: 2. Additionally and optionally, the isolated aptamer may further comprise a second and third polynucleotide sequences of SEQ ID NOs: 3 and 4 respectively disposed at the upstream and downstream of the fourth polynucleotide sequence, and thereby gives rise to a polynucleotide of SEQ ID NO: 6. According to preferred embodiments of the present disclosure, the polynucleotide of SEQ ID NO: 6 specifically binds to surface proteins of *Aggregatibacter actiomycetemcomitans* (*A. actiomycetemcomitans*).

In the second aspect of the present disclosure, a probe for detecting bacteria associated with periodontal disease is provided. The probe has a body, in which at least one part of the body is impregnated with the present isolated aptamer described above. Additionally and optionally, the present isolated aptamer is further conjugated with gold nanoparticles or is biotinylated.

According to one preferred embodiment of the present disclosure, one part of the body of the probe is impregnated with the present isolated aptamer, which is conjugated with gold nanoparticles, whereas another part of the body of the probe is impregnated with the present isolated aptamer, which is biotinylated. Preferably, the present isolated aptamer has a polynucleotide sequence at least 85% identical to SEQ ID NOs: 5 or 6, and if one part of the body of the probe is impregnates with the aptamer conjugated with gold nanoparticles, then the other part of the body of the probe is impregnated with the biotinylated aptamer.

According to embodiments of the present disclosure, the bacteria associated with periodontal disease are *P. gingivalis* or *A. actiomycetemcomitans*.

In the third aspect, a kit for detecting, in a sample obtained from the mouth of a subject, bacteria associated with periodontal disease. The kit comprises, the probe of the present disclosure; and an amplifying agent or an enzyme for amplifying signals of the isolated aptamer.

According to embodiments of the present disclosure, one part of the body of the probe is impregnated with the present isolated aptamer, which is conjugated with gold nanoparticles, whereas another part of the body of the probe is impregnated with the present isolated aptamer, which is biotinylated. Preferably, the present isolated aptamer has a polynucleotide sequence at least 85% identical to SEQ ID NOs: 5 or 6, and if one part of the body of the probe is impregnates with the aptamer conjugated with gold nanoparticles, then the other part of the body of the probe is impregnated with the biotinylated aptamer.

According to embodiments of the present disclosure, the enzyme may be avidin or streptavidin, and may amplify the signals of the biotinylated aptamer.

According to embodiments of the present disclosure, the amplifying agent may amplify the signals of the isolated aptamer conjugated with gold nanoparticles, and comprises:

a surfactant of formula (I): $NR_1R_2R_3R_4{}^+X^-$, wherein
$R_1$ is $C_{12-22}$ alkyl;
$R_2$, $R_3$, and $R_4$ are independently $C_{1-3}$ alkyl; and
$X^-$ is any of fluoride, chloride, bromide or iodide;
a colloid Au precursor; and
a reducing agent.

According to embodiments of the present disclosure, in the surfactant of the formula (I), $R_1$ is cetyl; $R_2$, $R_3$, and $R_4$ are independently methyl; and $X^-$ is chloride.

According to embodiments of the present disclosure, the reducing agent is any of vitamin A, vitamin C, vitamin E, or a combination thereof. In one example, the reducing agent is vitamin C.

According to embodiments of the present disclosure, the colloid Au precursor is $HAuCl_4$.

In the fourth aspect, a method of detecting, in a sample obtained from a gum pocket of a tooth of a subject, bacteria associated with periodontal disease is provided. The method comprises:

contacting the sample with the probe of the present disclosure; and detecting on the probe, complexes formed by the present isolated aptamer and the bacteria associated with a periodontal disease, as an indication of the presence of the bacterial associated with periodontal disease in the sample.

According to embodiments of the present disclosure, the sample taken from the gum pocket is sublingival plaque or gingival cervicular fluid.

According to embodiments of the present disclosure, the present isolated aptamer is further conjugated with gold nanoparticles or is biotinylated.

According to embodiments of the present disclosure, the method further comprises applying an amplifying agent to the complexes of the present isolated aptamer conjugated with gold nanoparticles and the bacteria associated with periodontal disease, in which the amplifying agent comprises:

a surfactant of formula (I): $NR_1R_2R_3R_4{}^+X^-$, wherein
$R_1$ is $C_{12-22}$ alkyl;
$R_2$, $R_3$, and $R_4$ are independently $C_{1-3}$ alkyl; and
$X^-$ is any of fluoride, chloride, bromide or iodide;
a colloid Au precursor; and
a reducing agent.

According to embodiments of the present disclosure, in the surfactant of the formula (I), $R_1$ is cetyl; $R_2$, $R_3$, and $R_4$ are independently methyl; and $X^-$ is chloride.

According to embodiments of the present disclosure, the reducing agent is any of vitamin A, vitamin C, vitamin E, or a combination thereof. In one example, the reducing agent is vitamin C.

According to embodiments of the present disclosure, the colloid Au precursor is $HAuCl_4$.

According to embodiments of the present disclosure, the method further comprises applying an enzyme, which may be avidin or streptavidin, to the complexes of the present isolated aptamer, which is biotinylated.

According to embodiments of the present disclosure, the present method is capable of detecting as low as 10 of the bacteria associated with periodontal disease.

According to embodiments of the present disclosure, the amplifying agent is capable of amplifying the signals of the complexes by at least 1,000 folds.

Based on the detection result determined in a gum pocket of a tooth of a subject described in the fourth aspect, proper medicament may then be administered to the subject to treat periodontal disease. Accordingly, it is a fifth aspect of the present disclosure to provide a method for treating periodontal disease in a subject. The method comprises administering a bactericide or an anti-microbial phototherapy to the gum pocket of the subject.

According to some embodiments the present disclosure, an effective amount of a bactericide is administered to the gum pocket to eradicate the bacteria associated with periodontal disease. Examples of bactericide suitable for use in the present method include, but are not limited to, hypochlorous acid, sodium lauroylsarcosine, isopropyl methylphenol, cetylpyridinium chloride, doxycycline, and a combination thereof.

Additionally or optionally, the method further comprises administering an anti-inflammatory agent concurrently with or after the administration of the bactericide to the gum pocket of the tooth. Examples of the anti-inflammatory agent include, but are not limited to, β-glycyrrhetinic acid, ε-aminocaproic acid, and a combination thereof.

According to some embodiments the present disclosure, the method comprises administering an anti-microbial phototherapy to the gum pocket of the subject. The anti-microbial phototherapy comprises steps of:

(i) administering a photosensitizer to the gum pocket of the tooth;

(ii) capping the tooth with a dental crown; and (iii) irradiating the gum pocket with a light having a wavelength between 700-2,500 nm.

According to preferred embodiments of the present disclosure, the photosensitizer is indocyanine green, and the light has the wavelength of 800 nm.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1A:
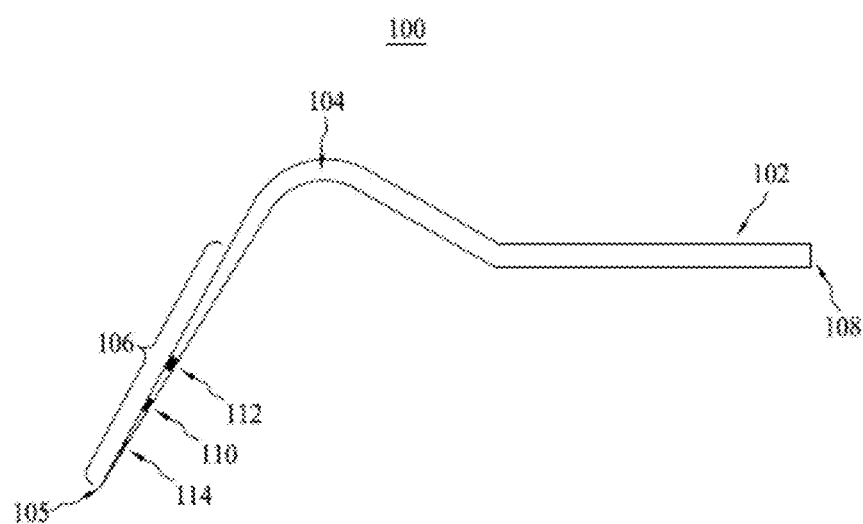
FIGS. 1A and 1B are schematic drawings respectively depicting probes for detecting bacteria associated with periodontal disease in accordance with embodiments of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise.

The term "aptamer" refers to a nucleic acid that is able to strongly and specifically bind to a surface protein of a periodontal pathogen. The aptamer of the present disclosure may be constituted by DNAs alone, RNAs alone, or DNAs and RNAs in combination. Optionally, the aptamer of the present disclosure may further comprise non-natural nucleotide(s). The "non-natural nucleotide" refers to an artificially constructed or artificially chemically modified nucleotide that is similar in property and/or structure to the natural nucleotide. Examples of the non-natural nucleotide include abasic nucleoside, arabinonucleoside, 2'-deoxyuridine, α-deoxyribonucleoside, β-L-deoxyribonucleoside, and other glycosylated nucleosides. The glycosylated nucleosides include glycosylated nucleosides having substituted pentose (2'-O-methylribose, 2'-deoxy-2'-fluororibose, 3'-O-methylribose, or 1',2'-deoxyribose), arabinose, substituted arabinose sugar, substituted hexose, or alpha anomer. The non-natural nucleoside of the present disclosure may be an artificially constructed base analog or an artificially chemically modified base. Examples of the "base analog" include a 2-oxo(H)-pyridin-3-yl group, a 5-substituted 2-oxo(1H)-pyridin-3-yl group, a 2-amino-6-(2-thiazolyl)purin-9-yl group, and a 2-amino-6-(2-oxazolyl)purin-9-yl group. Examples of the "modified base" include modified pyrimidine (e.g., 5-hydroxycytosine, 5-fluorouracil and 4-thiouracil), modified purine (e.g., 6-methyladenine and 6-thioguanosine), and other heterocyclic bases.

The term "sequence identity" as used herein, is generally expressed as a percentage and refers to the percent of nucleotides that are identical as between two sequences when optimally aligned. For the purposes of this invention, sequence identity means the sequence identity determined using the well-known Basic Local Alignment Search Tool (BLAST), which is publicly available through the National Cancer Institute/National Institutes of Health (Bethesda, Md.). Percentage of sequence identity is calculated by comparing two optimally aligned sequences over a window of comparison, determining the number of positions at which the identical nucleic acid base occurs in both sequences to yield the number of matched positions, dividing the number of matched positions by the total number of positions in the window of comparison, and multiplying the result by 100 to yield the percentage of sequence identity. In the present disclosure, when a nucleic acid is described to be identical to another nucleic by certain percentage (e.g., 85% identical), it means the two nucleic acids share a sequence identity of that certain percentage (i.e., sequence identity of 85%). In some examples, the present aptamer has a polynucleotide sequence that is at least 85% identical to SEQ ID NO: 5, which means the present aptamer and the polynucleotide of SEQ ID NO: 5 share a sequence identity of 85%. In other examples, the present aptamer has a polynucleotide sequence at least 85% identical to SEQ ID NO: 6, which means the present aptamer and the polynucleotide of SEQ ID NO: 6 share a sequence identity of 85%.

The term "periodontal disease" as used herein is interpreted in its broadest sense m to encompass diseases such as periodontitis, peri-implantatis (in which the tissue supporting the implant is disintegrated) and other forms of periodontal diseases and conditions.

The term "periodontal pathogens" as used herein refer to pathogenic bacteria commonly found in the oral cavity and in the pocket between a tooth and the gum, such as *Porphyromonas gingivalis, Bacteroides forsythus, Aggregati-* bacter actiomycetemcomitans, *Actinobacillus actinomycetemcomitans*, *Triponema denticola* and *Prevotella intermedia*. These bacteria need certain growth conditions and presence of nutrients to become active, and an active bacteria produces virulent products (e.g., toxins and enzymes) to aid its survival. These virulent products would also trigger inflammatory response in a host. In some examples, the periodontal pathogens refer to *Porphyromonas gingivalis* (*P. gingivalis*). In other examples, the periodontal pathogens are *Aggregatibacter actiomycetemcomitans* (*A. actiomycetemcomitans*)

2. The Present Aptamer

The first aspect of the present disclosure aims to provide novel aptamers that bind specifically and strongly to surface proteins of periodontal pathogens, such as *Porphyromonas gingivalis* (*P. gingivalis*) and *Aggregatibacter actiomycetemcomitans* (*A. actiomycetemcomitans*).

The aptamer of the present disclosure corresponds to, as described above in the "Definition" section, a natural nucleic acid such as DNA, RNA or a combination thereof. Also, the nucleic acid may partially or wholly comprises non-natural nucleotide. Preferably, the aptamer of the present disclosure is a DNA aptamer.

According to embodiments of the present disclosure, the aptamer may intramolecularly comprise one or more double-stranded regions. The "double-stranded region" refers to a region formed by consecutive base pairs between the nucleotide to strands constituting the nucleic acid molecular. The length of the consecutive base pairs is 2 to 10 bp, such as 2 to 5 bp, 2 to 6 bp, 2 to 7 bp, 2 to 8 bp, 2 to 9 bp or 2 to 10 bp. The aptamer may comprise two or more double-stranded regions. In such case, each doubled stranded region is constituted by base pairs that are the same or different between the double-stranded regions. Each double-stranded region may be interrupted by a region (such as mismatch sites, gaps, and internal loop structures) that is not base-paired between the strands. Alternatively, each double stranded region may be continuous.

The present aptamer may bind to a target substance, which refers to a polypeptide (preferably, a protein) on the surface of a pathogen (i.e., periodontal pathogen) that can serve as a target to which the aptamer may bind. The present aptamer is not particularly limited by its length, as long as it allows the aptamer to bind to surface proteins of periodontal pathogens. The length of each nucleotide strand of the present aptamer may range from 50 to 80 mer, such as 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80 mer; preferably 52 to 72 mer, such as 52, 53, 54, 55, 56, 57, 58, 59, 60, 61, 62, 63, 64, 65, 66, 67, 68, 69, 70, 71, and 72mer; more preferably 55 to 65 mer, such as 55, 56, 57, 58, 59, 60, 61, 62, 63, 64, and 65 mer. The base-paired strands do not have to have the same length, in other words, one strand may be longer or shorter than the other strand. In such case, the longer strand may form a hairpin structure through intramolecular annealing in a single-stranded region that is not matched to the other strand. A stem region formed in the hairpin structure is also encompassed in the double-stranded region of the present disclosure.

Each nucleotide strand of the present aptamer may contain a single-stranded region that is not base-paired with the other strand at the 5'-end and/or 3'-end of the double-stranded region. The double-stranded nucleic acid also encompasses a dumbbell-shaped nucleic acid in a closed ring form in which both nucleotide strands are linked via loop structure formed by the single-stranded regions. Such dumbbell-shaped nucleic acid is preferred as the nucleic acid molecule of the present disclosure, for its resistance to degradation by a nuclease, compared with the linear double-stranded nucleic acid.

According to embodiments of the present disclosure, the present aptamer has a binding affinity towards surface protein(s) of a periodontal pathogen, which refers to periodontal pathogens as described above in the "Definition" section.

In some embodiments, the present aptamer is a nucleic acid that comprises a first polynucleotide sequence of SEQ ID NO: 1. Additionally and optionally, the present aptamer may further comprise a second and third polynucleotide sequences of SEQ ID NOs: 3 and 4, respectively disposed at the upstream and downstream of the first polynucleotide sequence, thereby give rise to a polynucleotide of SEQ ID NO: 5.

In other embodiments, the present aptamer is a nucleic acid that comprises a fourth polynucleotide sequence of SEQ ID NO: 2, Additionally and optionally, the present aptamer may further comprise a second and third polynucleotide sequences of SEQ ID NOs: 3 and 4, respectively disposed at the upstream and downstream of the fourth polynucleotide sequence, thereby give rise to a polynucleotide of SEQ ID NO: 6.

Preferably, the present aptamer has a polynucleotide sequence at least 85% identical to SEQ ID NOs: 5 or 6. For example, the present aptamer is 85%, 86%, 87%, 88%, 89%, 90%, 91%, 92%, 93%, 94%, 95%, 96%, 97%, 98%, 99% or 100% identical to SEQ ID NOs: 5 or 6.

Figure 2A:
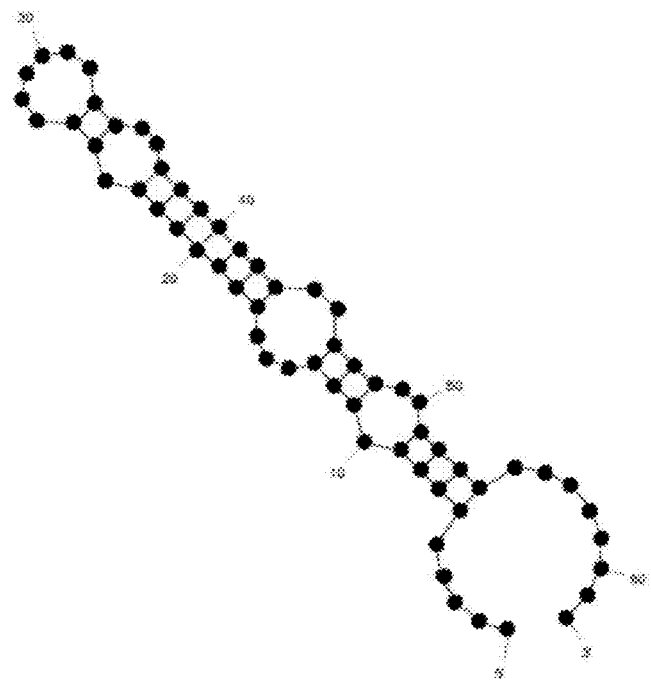
FIG. 2A and FIG. 2B are schematic drawings respectively depicting the secondary structure of the present aptamer of SEQ ID NO: 5 (FIG. 2A) and SEQ ID NO: 6 (FIG B) in accordance with one embodiment of the present disclosure.

According to one preferred embodiment of the present disclosure, the aptamer has a polynucleotide sequence 100% identical to SEQ ID NO: 5, which is 62 mer in length and binds to surface proteins of *Prophyromonas gingivalis* (*P. gingivalis*). In such case, the aptamer polynucleotide comprises 4 double-stranded regions respectively formed by 2, 7, 3, and 4 bps, with each double-stranded regions being interrupted by mismatched sites thereby forming 5 intramolecular loop structures and two single-stranded regions at the 3'- and 5'-ends of the polynucleotide (see FIG. 2A).

Figure 2B:
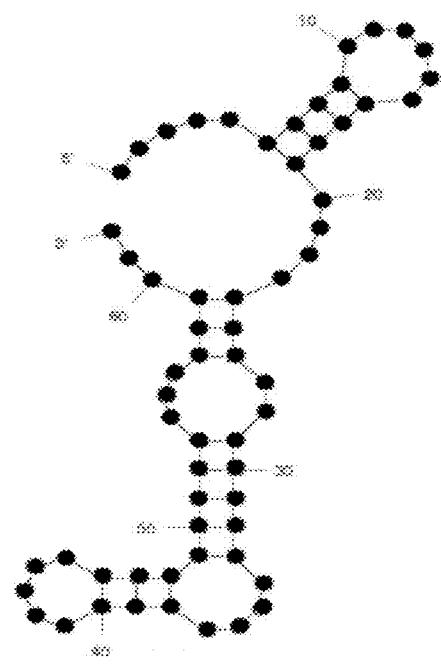

According to another preferred embodiment, the present aptamer has a polynucleotide sequence 100% identical of SEQ ID NO: 6, which is 62 mer in length and binds to surface proteins of *Aggregatibacter actiomycetemcomitans* (*A. actiomycetemcomitans*). In such case, the aptamer polynucleotide comprises 4 double-stranded regions respectively formed by 3, 5, 3, and 4 bps, with each double-stranded regions being interrupted by mismatched sites thereby forming 5 intramolecular loop structures and two single-stranded regions at the 3'- and 5'-ends of the polynucleotide (see FIG. 2B).

3. The Present Probe and Kit Comprising the Same

In the second aspect of the present disclosure, a probe for detecting bacteria associated with periodontal disease is provided.

Figure 1B:
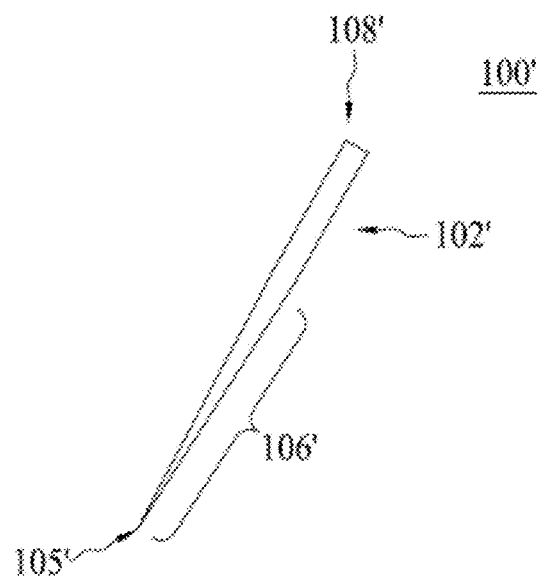

Reference is made to FIG. 1A, which is a schematic drawing of a probe 100 in accordance with one embodiment of the present disclosure. The probe 100 has an elongated body 102, in which one part of the body 102 is bent to provide an angular extension 104, which is again bent in opposite direction to form a tapered portion 106 that ends with a tip 105, while the other end of the body 102 remains un-tapered, un-bent, and blunt (i.e., the blunt end 108). The angular extension 104 in the probe 100 allows the user more room to work during operation (i.e., taking sample from a gum pocket), however, it is an optional feature. Reference is made to FIG. 1B, which depicts another embodiment of the present probe. Unlike the probe 100 depicted in FIG. 1A, the probe 100' in this embodiment does not comprise an angular extension in its body 102'. As depicted, the body 102' gradually tapers towards one direction thereby forming a taper portion 106 that ends with a tip 105', while the other end of the body 102' remains un-tapered and blunt (i.e., the blunt end 108').

Referring back to FIG. 1A, the tapered portion 106 may be impregnated with agents suitable for detecting periodontal pathogens, such as at least one of the present aptamer described above. For example, one part of the tapered portion 106 (i.e., part 110) is impregnated with the aptamer that binds to surface proteins of *P. gingivalis*, while the other part of the tapered portion 106 (i.e., part 112) is impregnated with the aptamer that binds to surface proteins of *A. actiomycetemcomitans*; by such manner, the probe 100 may simultaneously detect both *P. gingivalis* and *A. actiomycetemcomitans* from one sample. Optionally or in addition, one part of the tapered portion 106 (i.e., part 114) is impregnated with a buffer solution as a reference point during operation. Accordingly, at least some parts of the probe (e.g., the tapered portion 106) are preferably made of porous material that absorbs the present aptamer(s) and/or detecting agents therein. For example, at least the tapered portion 106 of the body 102 is made of cellulose or fibered material, whereas the rest of the body of the probe (such as the non-bended part of the probe, including the blunt end 108) may be made of a rigid material (e.g., plastic, wood, and etc) that allows an easy grip by the user during operation.

In practice, the dentist or dental hygienist may use the tapered portion 106 of the probe 100, particularly the tip 105, to take samples directly out from oral cavity or from pocket between a suspected tooth and the gum of the patient (i.e., a gum pocket). The probe is then subject to qualitative analysis, such as chromogenic test, enzyme linked immunoabsorbent assay (ELISA) and etc., so as to allow the bacteria-bound aptamers on the probe to be visualized via naked eyes or under suitable device. Accordingly, the present aptamer is further conjugated with agents that allow for visualization of the bacteria-bound aptamer. In some examples, the present aptamer is further conjugated with gold nanoparticles. In other examples, the present aptamer is biotinylated.

Optionally or in addition, prior to the qualitative analysis, suitable agents may be applied onto the parts (110, 112) of the tapered portion 106 of the probe 100, to amplify the signals of the bacteria-bound aptamers, so that the bacteria-bound aptamers on the probe 100 may be seen via naked eyes or using suitable device. According to some embodiments, an amplifying agent comprising colloidal gold precursors is applied onto the parts (110, 112) of the tapered portion 106 to amplify signals of the aptamers conjugated with gold nanoparticles; whereas an enzyme (e.g., streptavidin or avidin) is applied to the parts (110, 112) of the tapered portion 106 to amplify signals of the aptamers that are biotinylated. The formation of the complex of the bacterial and the gold nanoparticles conjugated aptamer and/or the complex of the bacterial and biotinylated aptamer on the probe 100, indicates the presence of bacteria associated with periodontal disease (e.g., *P. gingivalis, A. actiomycetemcomitans* or both) in the sample taken from the oral cavity of the patient.

The present disclosure thus also compasses a kit for detecting, in a sample obtained from the mouth of a subject, bacteria associated with periodontal disease. The kit may comprise, the probe of the present disclosure; an amplifying agent and an enzyme (e.g., avidin or streptavidin) described above for amplifying signals of the present aptamer. The kit may further comprise a label or package insert on or associated with the kit. The label or package insert indicates that the probe is for detecting bacteria associated with periodontal disease. Alternatively or additionally, the kit may further comprise a buffer, such as a phosphate-buffered saline, or a Ringer's solution. The kit may further include directions for how to amplify the signals of the present aptamer on the probe by use the accompanied amplifying agent and enzyme in the kit.

According to one embodiment, the kit may include, at least, (a) a first container containing the present probe; and optionally, (b) a second container containing the amplifying agent; optionally, (c) a third container containing the enzyme (i.e., streptavidin or avidin); optionally, (c) a fourth container containing a buffer, and (c) a legend associated with the kit for instructing a user how to use the kit. The legend may be in a form of pamphlet, tape, CD, VCD or DVD.

4. The Method of Detecting Periodontal Pathogens

In the fourth aspect, a method of detecting, in a sample obtained from the mouth (e.g., a gum pocket of a tooth) of a subject, bacteria associated with periodontal disease is provided. The method comprises:
contacting the sample with the probe of the present disclosure; and
detecting on the probe, complexes of the present isolated aptamer and the bacteria associated with a periodontal disease, as an indication of the presence of the bacterial associated with periodontal disease in the sample.

According to embodiments of the present disclosure, a sample of sublingual plaque or gingival cervicular fluid is taken from the oral cavity (i.e., a gum pocket) of a human by use of the tapered end of the probe described above, in which at least one part of the tapered end is impregnated with the present aptamer.

Additionally and optionally, the present aptamer (e.g., SEQ ID NOs: 5 or 6) is further conjugated with gold nanoparticles, or is biotinylated. After contacting the sample, the probe is left stand for a sufficient period of time to allow formation of the complex of the bacteria and gold nanoparticles conjugated aptamer or the complex of the bacteria and biotinylated aptamer. Additionally and optionally, the signal of the bacteria bound-aptamer may be amplified to allow visualization of the complex via naked eyes. For example, the probe may be further treated with an amplifying agent comprising colloid Au precursor, which amplifies the signal of aptamer conjugated with gold nanoparticles; while avidin or streptavidin may be added to amplify the signal of biotinylated aptamer.

According to embodiments of the present disclosure, the amplifying agent comprises:
a surfactant of formula (I): $NR_1R_2R_3R_4^+X^-$, wherein
$R_1$ is $C_{12-22}$alkyl,
$R_2$, $R_3$, and $R_4$ are independently $C_{1-3}$alkyl; and
$X^-$ is any of fluoride, chloride, bromide or iodide;
a colloid Au precursor; and
a reducing agent.

According to embodiments of the present disclosure, in the surfactant of the formula (I), $R_1$ is cetyl; $R_2$, $R_3$, and $R_4$ are independently methyl; and $X^-$ is chloride.

According to embodiments of the present disclosure, the reducing agent is any of vitamin A, vitamin C, vitamin E, or a combination thereof. In one example, the reducing agent is vitamin C.

According to embodiments of the present disclosure, the colloid Au precursor is $HAuCl_4$.

According to embodiments of the present disclosure, the present method is capable of detecting as low as 10 of the bacteria associated with periodontal disease.

According to embodiments of the present disclosure, the amplifying agent is capable of amplifying the signals of the complexes by at least 1,000 folds.

5. The Method of Treating Periodontal Disease

Based on the presence of periodontal pathogens detected by the method described above, proper treatment may be administered to the subject to alleviate or ameliorate symptoms associated with periodontal disease. Accordingly, it is the fifth aspect of the present disclosure to provide a method of treating periodontal disease of a subject. The method comprises administering a bactericide or an anti-microbial phototherapy to the gum pocket of the subject.

In some embodiments, an effective amount of a bactericide is administered to the gum pocket to eradicate the bacteria associated with periodontal disease. Examples of bactericide suitable for use in the present method include, but are not limited to, hypochlorous acid, sodium lauroylsarcosine, isopropyl methylphenol, cetylpyridinium chloride, doxycycline, and a combination thereof. In preferred examples, a combination of sodium lauroylsarcosine, isopropyl methylphenol, and cetylpyridinium chloride is administered to the gum pocket to eradicate the bacteria associated with periodontal disease.

Alternatively or optionally, an anti-inflammatory agent may be administered concurrently with or after the administration of the bactericide. Examples of the anti-inflammatory agent include, β-glycyrrhetinic acid, ε-aminocaproic acid, and the like.

Alternatively or optionally, the bactericide may be administered several times until the periodontal pathogens are completely eradicated. For example, the bactericide may be administered at least 1, 2, 3, 4, 5, 6, 7, 8, 9, or 10 times, depends on the need of the subject. In some embodiments, the present method is repeated twice. In other embodiments, the present method is repeated 4 times.

According to other embodiments the present disclosure, the gum pocket of the subject is treated with an anti-microbial phototherapy. The anti-microbial phototherapy comprises steps of:

(i) administering a photosensitizer to the gum pocket of the tooth;

(ii) capping the tooth with a dental crown; and (iii) irradiating the gum pocket with a light having a wavelength between 400-2,500 nm.

According to embodiments of the present disclosure, the photosensitizer may be a contrast agent having a maximum absorption in the spectrum that ranges from 400 nm to 2,500 nm, such as 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1,000, 1,100, 1,200, 1,300, 1,400, 1,500, 1,600, 1,700, 1,800, 1,900, 2,000, 2,100, 2,200, 2,300, 2,400, and 2,500 nm. In some embodiments, the photosensitizer has an absorption maximum in the wavelength between 400 nm to 810 nm. In other embodiments, the photosensitizer has an absorption maximum in the wavelength between 700 nm to 2,500 nm.

In one preferred embodiment, the photosensitizer is indocyanine green (ICG), which an absorption maximum around 800 nm. Inventors of the present disclosure unexpected identify that upon being exposed to the light of 800 nm, ICG will emit active species such as NO that serves as a bactericide and kills periodontal pathogens in the gum pocket.

Alternatively or optionally, the photosensitizer may be in gel form.

Alternatively or optionally, the anti-microbial phototherapy may be repeated several times until the periodontal pathogens are completely eradicated. For example, the present method may be repeated at least 1, 2, 3, 4, 5, 6, 7, 8, 9, or 10 times, depends on the need of the subject. In some embodiments, the present method is repeated twice. In other embodiments, the present method is repeated 4 times.

The present invention will now be described more specifically with reference to the following embodiments, which are provided for the purpose of demonstration rather than limitation.

EXAMPLES

Materials and Methods

Culture of Periodontal Pathogens

*Porphyromonas gingivalis* (Pg) (ATCC® 33277™) were activated and cultured in the ATCC® Medium 2722 in an anaerobic chamber at 37° C. for at least 4 days before one colony was chosen and transferred to a new culture plate and continued cultured in the anaerobic chamber before use. *Aggregatibacter actiomycetemcomitans* (Aa) (ATCC® 29522™) were activated and cultured in the ATCC® Medium 44 in a chamber containing 5% $CO_2$ at 37° C. for 2 days before use. *Streptococcus mitis* (Sm) (ATCC®49456™) were activated and cultured in the solid ATCC® Medium 44 in a chamber containing 5% $CO_2$ at 37° C. for 24 hrs before use.

Preparation of DNA Aptamers

1. Selecting DNA Aptamers from the Aptamer Library

The oligonucleotide molecules capable of binding to surface proteins of periodontal pathogens were screened from a DNA library generated by MDBio, Inc (Taiwan, R.O.C.) using the method of Systematic evolution of ligands by exponential enrichment (SELEX), in which the SELEX-derived single stranded DNA molecules were selected against *P. gingivalis, A. actiomycetemcomitans* or *S. mitis*. Briefly, 10 μL of the SELEX-derived aptamers (about $10^{15}$ aptamers) were mixed with 90 μL of the SELEX buffer, the mixture was first heated at 95° C. for 2 mins, then cooled down to 39° C. at the rate of 2° C./min. A bacteria broth (500 μL, OD=0.6 to 0.7, containing about $1 \times 10^9$ bacteria) was mixed with the SELEX buffer, and the total volume was brought up to about 1,500 μL using the SELEX buffer. The mixture was loaded to a rotary mixer and rotary mixed at room temperature for about 30 min before subjected to centrifugation at 6,000×g for 5 min. The supernatant was discarded and the precipitate was re-suspended in 1,000 μL SELEX buffer, and centrifuged at 6,000×g for 5 min again. This step was repeated 5 times. The precipitate thus produced was re-suspended in 1,000 μL SELEX buffer and heated at 95° C. for 10 mins, the mixture was then subjected to centrifugation at 6,000×g for 5 min, and the supernatant was collected.

2. Amplified the Selected DNA Aptamers by Polymerase Chain Reaction (PCR)

The selected aptamers were mixed with PCR reagents and heated at 94° C. for 2 min, at 94° C. for 30 sec, at 57° C. for 30 sec, and at 72° C. for 20 sec. The PCR product was then purified and cloned by use of suitable vector.

After selection and amplification by SELEX and PCR, respectively, a product of 62 bp against *P. gingivalis* was identified, which has a polynucleotide sequence of SEQ ID NO: 5. Similarly, a product of 62 bp against *A. actiomycetemcomitans* was also identified, which has a polynucleotide sequence of SEQ ID NO: 6. The computer simulated secondary structures of SEQ ID NOs: 5 and 6 are respectively provided in FIGS. 2A and 2B.

Determining the Binding Affinity and/or Specificity of the DNA Aptamers by Real-Time Qualified Polymerase Chain Reaction.

1. Binding Affinity

The aptamers (48.8 pM) were mixed with the same amount of a bacteria (i.e., *P. gingivalis*, *A. actiomycetemcomitans* or *S. mitis*), and the mixture (1,500 μL) was then rotary mixed at room temperature for 30 min, then centrifuged at 6000×g for 5 min. The supernatant was discarded, and the precipitate was re-suspended in 1,000 μL using SELEX buffer. Repeated the treatment for 5 times. The precipitate thus produced was re-suspended in 1,000 μL SELEX buffer and heated at 95° C. for 10 mins, the mixture was then subjected to centrifugation at 6,000×g for 5 min, and the supernatant was collected. Then amplified the product by real time qualitied polymerase chain reaction (RQPCR) and the amplified product is separated by electrophoresis in accordance with their respective molecular weight.

2. Binding Specificity

The aptamers (12.5 nM) were mixed with the same amount of a bacteria (i.e., *P. gingivalis*, *A. actiomycetemcomitans* or *S. mitis*), and rotary mixed at room temperature for 30 min. The mixture was centrifuged at 6000×g for 5 min, discarded the supernatant and re-suspended the precipitate in SELEX buffer. Repeated the centrifugation treatment 5 times, and finally re-suspended the precipitate in 1,000 μL SELEX buffer. The mixture was heated at 95° C. for 10 mins, then subjected to centrifugation at 6,000×g for 5 min, and the supernatant was collected. The harvested aptamers were then PCR amplified and separated by electrophoresis in accordance with their respective molecular weight.

Capturing the Periodontal Pathogens by Gold Nanoparticles Conjugated Aptamers

Gold nanoparticles were prepared by reducing tetrachloroauric acid ($HAuCl_4$) with sodium citrate. The thus produced gold nanoparticles ($1 \times 10^{-7}$) were conjugated to primers of the SH-modified aptamers (authorized synthesis provided by MDBi, Inc. (Taipei, Taiwan)) in a molar ratio of 1:1,000, and the un-conjugated primers were subsequently removed by centrifugation. The precipitate was collected and mixed with a bacteria solution ($1 \times 10^9$). The mixture was then loaded into a rotary mixer and the conjugation was allowed to proceed for 1 hr at room temperature, the non-conjugated gold nanoparticles were removed by centrifugation. The conjugated product was examined using Transmission Electron Microscopy (TEM).

Constructing High Sensitivity Side-Flow Detection Strips

Figure 5:
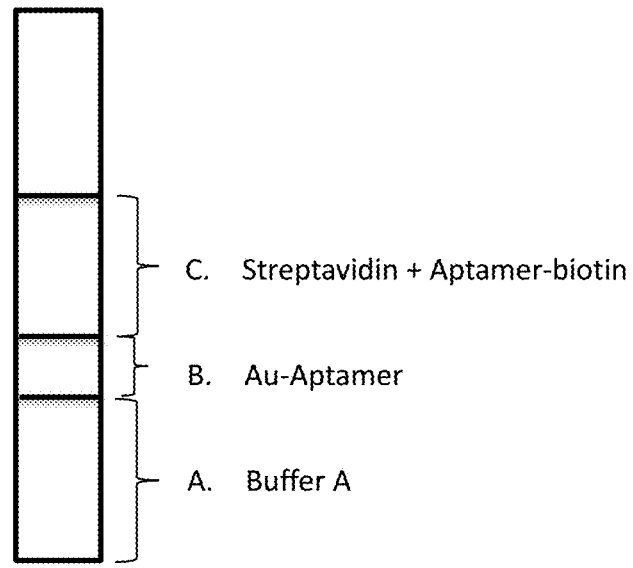
FIG. 5 is a schematic diagram of the high sensitivity side-flow detection strip constructed in accordance with one embodiment of the present disclosure, in which "A," "B," and "C" respectively denotes the areas on the detection strip that comprise the buffer, the gold nanoparticles conjugated aptamer of *P. gingivalis*, and the streptavidin and biotinylated aptamer of *P. gingivalis* complex.

On three different strips, respectively applied 100 μL of the gold nanoparticles conjugated aptamers onto one area (designated as "B area") of a glass fiber strip, 100 μL of buffer A (i.e., 1% BSA) onto one area of a Cellulose Fiber Sample Pad (designated as "A area"), and 0.6 μL of the Streptavidin and aptamer-biotin complex (authorized synthesis provided by MDBi, Inc. (Taipei, Taiwan)) onto one area of Hi-Flow Plus 135 Membrane Cards (designated as "C area). The three strips were then glued together to form a detection strip that was 0.4 cm in width. A schematic diagram of the thus constructed detection strip is depicted in FIG. 5, in which the areas respectively designated as "A," "B," and "C" had adsorbed thereon "buffer A," "gold nanoparticles conjugated aptamer," and "the Streptavidin and aptamer-biotin complex" as described above.

Preparation of an Amplifying Agent

In a container, mixed 9 mL water, 0.36 g cetyl trimethyl ammonium bromide, and 1 mL $HAuCl_4$ (5 mM), stirred the mixture until a golden clear solution was produced; then add 600 mL vitamin C (100 mM), mixed thoroughly until a colorless clear solution was obtained.

Example 1 Determining the Binding Affinity and Specificity of the Present Aptamer to Periodontal Pathogens In this example, the binding affinity and specificity of the selected aptamers to periodontal pathogens were determined in accordance with procedures described in the "Materials and Methods" section. Results are provided in FIG. 3.

Figure 3A:
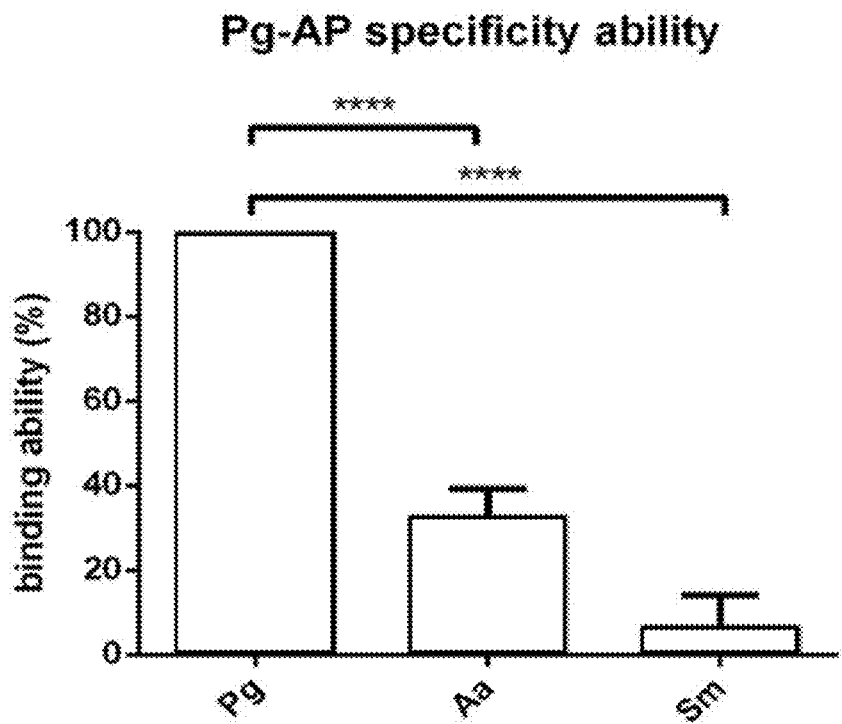
FIG. 3A is a bar graph depicting the binding specificity of the aptamer of *P. gingivalis* against *P. gingivalis, A. actiomycetemcomitans* or *S. mitis* in accordance with one embodiment of the present disclosure.
Figure 3B:
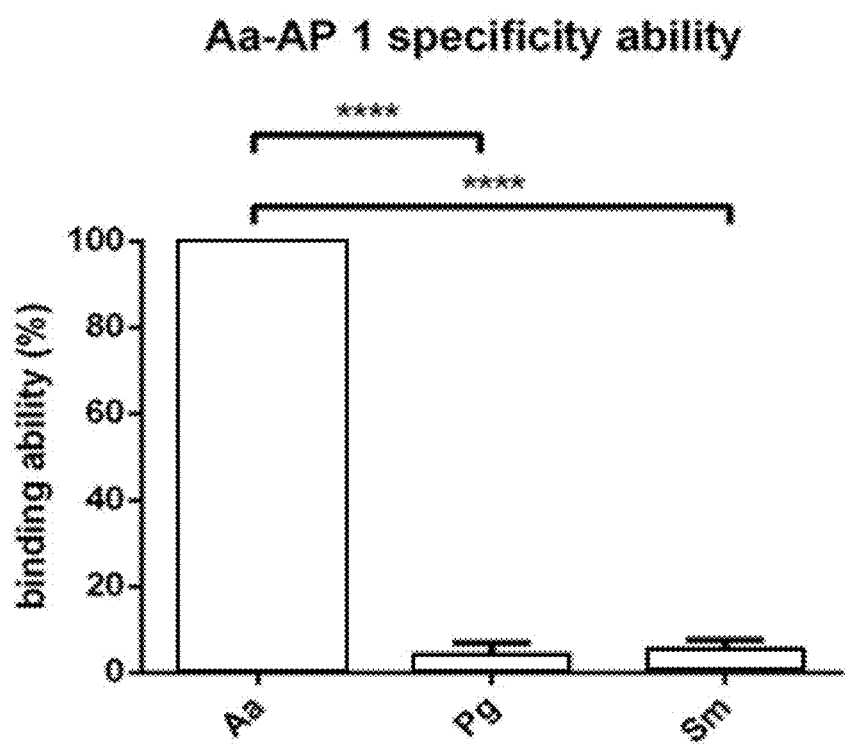
FIG. 3B is a bar graph depicting the binding specificity of the aptamer of *A. actiomycetemcomitans* against *A. actiomycetemcomitans, P. gingivalis,* or *S. mitis* in accordance with one embodiment of the present disclosure.

As illustrated in FIG. 3, the selected aptamer having SEQ ID NO: 5 exhibited higher binding specificity toward *P. gingivalis* (Pg) ($Kd=4.592$ nM) than to *A. actiomycetemcomitans* (Aa) or *S. mitis* (Sm) (FIG. 3A); whereas the selected aptamer having SEQ ID NO: 6 was more specificity toward *A. actiomycetemcomitans* (Aa) ($Kd=3.503$ nM) than to *P. gingivalis* (Pg) or *S. mitis* (Sm) (FIG. 3B).

Example 2 Capturing *P. gingivalis* and *A. actiomycetemcomitans* by Gold Nanoparticles Conjugated Aptamers In this example, the selected aptamers of SEQ ID NO: 5 or 6 were first conjugated with gold nanoparticles, then were used to capture periodontal pathogens. Results are provided in TEM photographs of FIGS. 4A and 4B.

Figure 4A:
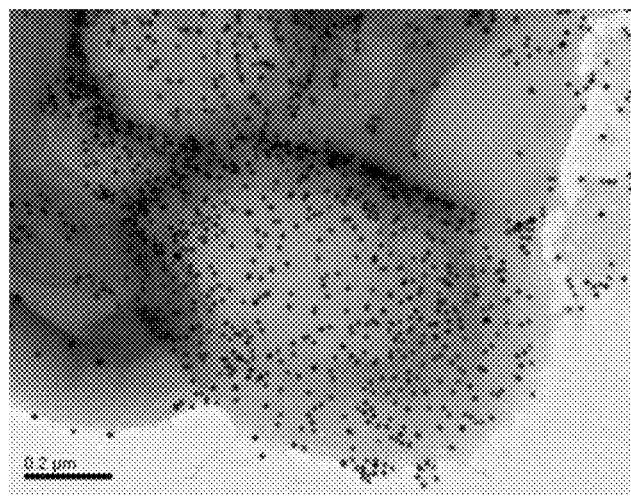
FIG. 4A is a TEM photograph depicting *P. gingivalis* having the gold nanoparticles conjugated aptamer of *P. gingivalis* bonded on its surface in accordance with one embodiment of the present disclosure.
Figure 4B:
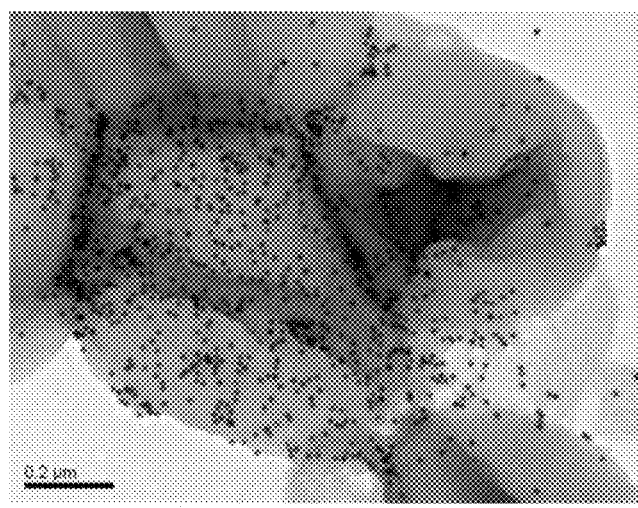
FIG. 4B is a TEM photograph depicting *A. actiomycetemcomitans* having the gold nanoparticles conjugated aptamer of *A. actiomycetemcomitans* bonded on its surface in accordance with one embodiment of the present disclosure.

FIG. 4A is TEM photograph of *P. gingivalis* captured by gold nanoparticles conjugated aptamers of SEQ ID NO: 5, and FIG. 4B is TEM photograph of *A. actiomycetemcomitans* captured by gold nanoparticles conjugated aptamers of SEQ ID NO: 6.

Example 3 Determining Cross Reactivity of the Present Aptamers Using High Sensitivity Side-Flow Detection Strips To test cross-reactivity, high sensitivity side-flow detection strips (see FIG. 5) were respectively constructed in accordance with procedures described in "Materials and Methods" section. In one set of detection strips, the gold nanoparticles conjugated aptamer of *P. gingivalis*, and the streptavidin and biotinylated aptamer of *P. gingivalis* complex were respectively fixed thereon, then, $10^9$ of *A. actiomycetemcomitans* were added to see if there were any cross-reaction. The result indicated minor cross reaction existed between the biotinylated aptamer of *P. gingivalis* (SEQ ID NO: 5) and *A. actiomycetemcomitans*. By similar manner, the strips for detecting cross-reactivity of the aptamer of *A. actiomycetemcomitans* (SEQ ID NO: 6) and *P. gingivalis* were constructed, and the results indicated that there was no cross reaction between the aptamer of *A. actiomycetemcomitans* (SEQ ID NO: 6) and *P. gingivalis* (SEQ ID NO: 5).

Example 4 Characterizing the Sensitivity of the Present Aptamers in Capturing Periodontal Pathogens

4.1 Determining the Sensitivity of the Present Aptamer of *A. actiomycetemcomitans*

In this example, detection strips were respectively loaded thereon with the present 3'- or 5'-biotinylated aptamer of *A. actiomycetemcomitans*, then various amounts of *A. actiomycetemcomitans* were applied onto the areas containing the aptamers.

Results indicated that the present aptamer was capable of detecting wide ranges of *A. actiomycetemcomitans*, i.e., from 10 to 1,000,000 *A. actiomycetemcomitans*; suggesting the present aptamer is highly sensitive in capturing *A. actiomycetemcomitans*.

4.2 Enhancing the Signal of the Present Aptamers Conjugated with Gold Nanoparticles In this example, an amplifying agent known to enhance the signal of gold nanoparticles was first further applied onto the detection spots of Example 4.1 to amplify the detection signals. The amplifying agent was prepared in accordance with steps described in "Materials and Methods" section. Results are summarized in Table 1.

TABLE 1

The effect of amplifying agent in the detection of *A. actiomycetemcomitans* or *P. gingivalis*

| | $10^9$ | $10^8$ | $10^7$ | $10^6$ | $10^5$ | $10^4$ | $10^3$ | $10^2$ | $10^1$ |
|---|---|---|---|---|---|---|---|---|---|
| | | | | | No. Bacteria | | | | |
| | | | | without amplifying agent | | | | | |
| A.a | + | + | + | + | + | − | − | − | − |
| P.g | + | + | + | + | − | − | − | − | − |
| | | | | with amplifying agent | | | | | |
| A.a | + | + | + | + | + | + | + | + | + |
| P.g | + | + | + | + | + | + | + | + | + |

+: visible by the naked eyes.
−: not visible by the naked eyes.

It is evident from the results, the sensitivity of the present aptamer of *A. actiomycetemcomitans* increased for at least 1,000 folds with the addition of the amplifying agent, in which the number of the bacteria previously undetected (i.e., $<10^6$) became detectable, even if the number of the bacteria was as low as 10.

Example 5 Detecting Periodontal Pathogens in Human Subjects Using the Present Aptamers In this example, mouth samples were taken from the surface of the teeth (including the front, behind or the chewing surface), between the teeth, and/or along the gumline, of five patients (i.e., patients 1 to 5) with informed written consent using detection probes of the present invention, which had been immobilized thereon with gold nanoparticles conjugated aptamer of *P. gingivalis*. Results are illustrated in FIG. 6.

Figure 6:
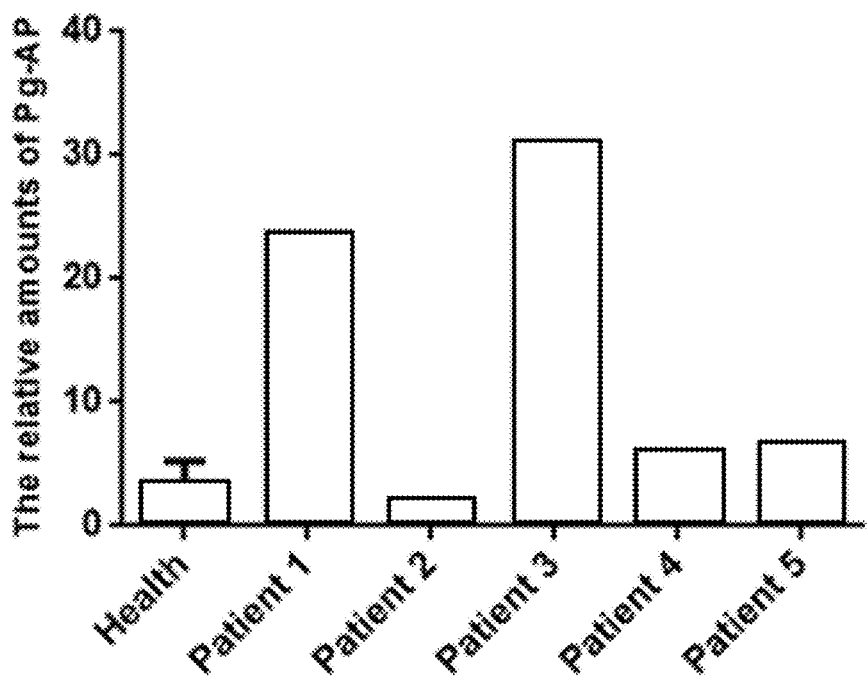
FIG. 6 illustrates the detection of *P. gingivalis* in samples obtained from healthy or periodontal subject using the present aptamer of *P. gingivalis* in accordance with one embodiment of the present disclosure.

Among the 5 patients, patients 1 and 3 were confirmed to have dental plaques, while patients 2, 4 and 5 did not (FIG. 6). In addition, patients 1 and 3 were further confirmed to have *P. gingivalis* present on their teeth, which suggested that patients 1 and 3 are in high risk of developing periodontal disease in the future.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

---

What is claimed is:

1. A method of detecting and treating periodontal disease in a subject comprising:
   detecting the presence of bacteria associated with the periodontal disease in a sample obtained from a gum pocket of a tooth of the subject, in which the detection comprises:
   (a) contacting the sample with a probe having an isolated aptamer impregnated therein, wherein the isolated aptamer has a polynucleotide sequence of SEQ ID NO: 5 or 6;
   (b) subjecting the probe in the step (a) to the treatment of an amplifying agent or an enzyme; and
   (c) detecting on the probe the presence of complexes formed by the isolated aptamer of SEQ ID NOs: 5 or 6 and bacteria associated with the periodontal disease, as an indication of the presence of the bacterial associated with periodontal disease in the sample; and
   treating the subject based on the detection of the step (c), in which the treatment comprises,
   (d) administering a bactericide or an anti-microbial phototherapy to the gum pocket of the subject, wherein
   the bactericide is a combination of sodium lauroylsarcosine, isopropyl methylphenol, and cetylpyridinium chloride; and
   the anti-microbial phototherapy comprises:
   (i) administering a photosensitizer to the gum pocket of the tooth;
   (ii) capping the tooth with a dental crown; and
   (iii) irradiating the gum pocket with a light having a wavelength between 700-2,500 nm.

2. The method of claim 1, wherein the isolated aptamer of SEQ ID NOs: 5 or 6 is biotinylated or is conjugated with gold nanoparticles.

3. The method of claim 1, wherein the probe has two isolated aptamers impregnated therein, provided that if one of the isolated aptamer is biotinylated, then the other isolated aptamer is conjugated with gold nanoparticles, and vice versa.

4. The method of claim 3, wherein in the step (b), the enzyme is streptavidin or avidin.

5. The method of claim 4, wherein the detection is capable of detecting as low as 10 of the bacteria associated with periodontal disease.

6. The method of claim 1, wherein in the step (b), the amplifying agent comprises:
a surfactant of formula (I): $NR_1R_2R_3R_4{}^+X^-$, wherein
$R_1$ is $C_{12-22}$alkyl;
$R_2$, $R_3$, and $R_4$ are independently $C_{1-3}$alkyl; and
$X^-$ is any of fluoride, chloride, bromide or iodide;
a colloid Au precursor; and
a reducing agent.

7. The method of claim 6, wherein in the formula (I), $R_1$ is cetyl; $R_2$, $R_3$, and $R_4$ are independently methyl; and $X^-$ is chloride.

8. The method of claim 6, wherein the reducing agent is any of vitamin A, vitamin C, vitamin E, or a combination thereof.

9. The method of claim 6, wherein the colloid Au precursor is $HAuCl_4$.

10. The method of claim 6, wherein the amplifying agent is capable of amplifying signals produced from the complexes by at least 1,000 folds.

11. The method of claim 1, further comprising administering an anti-inflammatory agent to the gum pocket of the tooth.

12. The method of claim 11, wherein the anti-inflammatory agent is β-glycyrrhetinic acid, ε-aminocaproic acid, or a combination thereof.

13. The method of claim 1, wherein the photosensitizer is indocyanine green; and the light has the wavelength of 800 nm.

14. The method of claim 1, wherein the sample is sublingual plaque or gingival cervicular fluid.

* * * * *